June 25, 1974 W. H. JESSEL. JR., ET AL Plant Pat. 3,576
CHRYSANTHEMUM PLANT
Filed Jan. 31, 1973
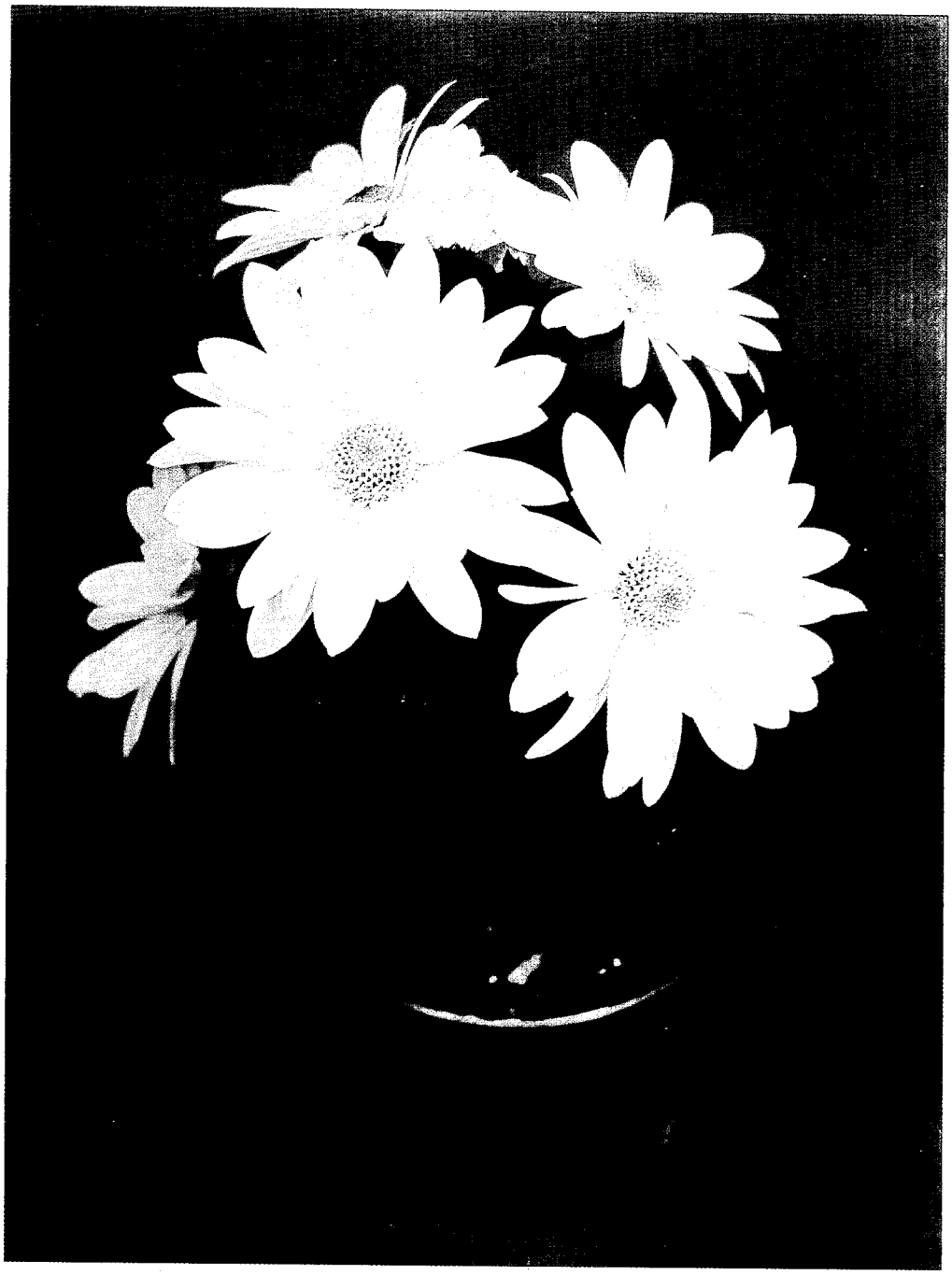

United States Patent Office

Plant Pat. 3,576

Patented June 25, 1974

3,576
CHRYSANTHEMUM PLANT

Walter H. Jessel, Jr., Doylestown, and William E. Duffett, Akron, Ohio, assignors to Yoder Brothers, Inc., Barberton, Ohio

Filed Jan. 31, 1973, Ser. No. 328,416
Int. Cl. A01h *5/00*
U.S. Cl. Plt.—74 1 Claim

The present invention comprises a new and distinct cultivar of daisy form chrysanthemum plant known by the varietal name Garland. The new cultivar is a seedling of #67100–55 × #67586–1. Both parents are unpatented and are identified for breeding purposes by the above breeding numbers.

The new cultivar is similar in many respects to the unpatented but commercially well known cultivar Bonnie Jean, having the same characteristics as Bonnie Jean of:

1. Capable of being grown as a pot mum using tall treatment, and as a cut daisy spray.
2. Similar flower size and daisy form.
3. Foliage color.
4. Prominent stipules at base of leaf.
5. Similar vigor.

The new cultivar is distinguished from Bonnie Jean by the following characteristics when grown under comparable conditions:

1. Its ivory white flower color, as compared with the more pure white color of Bonnie Jean.
2. A greater responsiveness to B–9 for growth control. It is 4″–5″ shorter with 4″ more spread when grown as a spray type pot mum in a 6″ pot with 4 cuttings, given one application of 2500 p.p.m. of B–9 approximately two weeks after pinching, and tall treatment as defined in the timetables of Yoder Brothers, Inc., Barberton, Ohio, for the various seasons.
3. Approximately 4–5 days earlier response, and 4–5 days shorter crop time.
4. Smaller and finer textured foliage.
5. A year round recommended period of use in the United States as compared to a recommended period of May through October in the northern United States for Bonnie Jean (grown as a syray pot).

6. An absence of pollen resulting in an improved keeping quality and homelife of 4–5 days, as well as ray petals that are not marred with pollen.
7. A greater uniformity of flowering response, even when buds are initiated under low (54°–56°) temperature.
8. No known foliar sensitivities to present day greenhouse chemicals.
9. Improved flower substance.
10. Improved form retention in low light periods.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environment conditions such as temperature, day length, and light intensity. Suggested flowering in the northern and western United States as a spray pot mum is from January through December; coastal California, January through December, and in southern Florida, October through April. Suggested flowering as a cut daisy spray in the northern and western United States is from May through October; coastal California, April through November 15, and in southern Florida, October through April.

The accompanying photographic drawing is a specimen photograph of the new cultivar by itself, with the color being as nearly true as possible with color illustrations of this type.

In the following description, color references are made to the Munsell Color Book, 1963 edition, and comparisons are made with the cultivar Bonnie Jean. Where a value or description appears only for the new cultivar, the same value or description applies to the cultivar Bonnie Jean.

Botanical classification: *Chrysanthemum morifolium*

| | Garland | Bonnie Jean |
|---|---|---|
| Bloom: | | |
| Size | 3″ | |
| Fully expanded | 3½″ | |
| Borne | Clusters on elongated pedicals | |
| Stems | Short and strong | |
| Form | Daisy | |
| Permanence | 12–14 days | 7–10 days. |
| Color (Munsel Cascade): | | |
| Center of flower | Yellow-green, 2.5GY6/8 to yellow, 7.5Y8/12 | Yellow-green, 2.5GY6/8 to yellow, 10Y8.5/10. |
| Base of petals | Light yellow-green, 2.5GY7/8 | Light yellow-green, 2.5GY7/8. |
| Inside of petals | Light yellow, 10Y9/4 to ivory white, 10Y9/1 | White, N9.5/. |
| Reverse of petals | Ivory, 10Y9/2 to ivory white, 10Y9/1 | Do. |
| Tonality from a distance | Ivory | White. |
| Discoloration | Ivory white, 10Y9/1 | White, N9.5/. |
| Petals: | | |
| Texture | Smooth | |
| Appearance and form | Open at base, shallow multiridge keel, tapers to a blunt notched tip with recurved petal edges. | Open at base, broadening quickly to a broad flat keel, slight longitudinal petal roll, tapering to a blunt tip. |
| Arrangement | Composite, whorled on a single receptacle | |
| Persistence | Resists shatter | |
| Fragrance | Typical chrysanthemum | |
| Reproductive organs: | | |
| Stamen, anthers | 250+ | |
| Pollen | None | |
| Arrangement | Clustered in center of flower, if present | Abundant. |
| Styles | Present both ray and disc florets | |
| Length | Short | |
| Ovaries | At the base of petal attached to receptacle | |
| Plant: | | |
| Form | Herbaceous | |
| Growth | Spreading | Semi-upright. |
| Height (cut) | Approximately 34″ to 38″ grown as a single stem cut flower, given 3–4 long day weeks and a total crop time of 12–13 weeks during the various seasons of recommended use (May through October) according to the timetables published by Yoder Brothers, Inc., Barberton, Ohio. | Approximately 34″ to 38″ grown as a single stem cut flower, given 3–4 long day weeks and a total crop time of 13–14 weeks during the various seasons of recommended use (May through October) according to the timetables published by Yoder Brothers, Inc., Barberton, Ohio. |

TABLE—Continued

| | Garland | Bonnie Jean |
|---|---|---|
| Height (pot) | Approximately 12″ to 15″ when grown as a pinched spray pot in a 4-cutting, 6″ pot given 1 application of 2500 p.p.m. B-9 approximately 2 weeks after pinching and 9 week tall treatment (1-2 weeks of long days) during the various seasons of recommended use (January through December) as defined in the timetables of Yoder Brothers, Inc., Barberton, Ohio. | Approximately 16″-20″ when grown as a pinched spray pot in a 4-cuttings, 6″ pot given 1 application of 2500 p.p.m. B-9 approximately 2 weeks after pinching and 10 week tall treatment (1-2 weeks of long days) during the various seasons of recommended use (April through November 15) as defined in the timetables published by Yoder Brothers, Inc., Barberton, Ohio. |
| Spread (pot) | Approximately 14″-16″ when grown as a pinched spray pot, in a 4-cutting, 6″ pot given 1 application of 2500 p.p.m. B-9 approximately 2 weeks after pinching and 9 week tall treatment (1-2 weeks of long days) during the various seasons of recommended use (January through December) as defined in the timetables published by Yoder Brothers, Inc., Barberton, Ohio. | Approximately 12″-14″ when grown as a pinched spray pot in a 4-cutting, 6″ pot given one application of 2500 p.p.m. B-9 approximately 2 weeks after pinching and 10 week tall treatment (1-2 weeks of long days) during the various seasons of recommended use (April through November 15) as defined in the timetables published by Yoder Brothers, Inc., Barbarton, Ohio. |
| Spread (cut | Slight to none | Slight to none. |
| Foliage: | | |
| Top side | Dark green, 7.5GY3/4 | |
| Size | Length to width ratio 16:11 with length up to 4″, and width up to 2¾″. | Length to width ratio 3:2 with length up to 8″ and width up to 4″. |
| Quantity | Numerus | |
| Shape | Spatulate lobed | |
| Texture | Smooth | Coarse. |
| Ribs and veins | Prominent | |
| Edge | Slightly indented | Deeply indented. |
| Serration | Fine | Moderate. |
| Under side | Medium green, 7.5GY5/4 | |
| Stipules | Prominent | |

We claim:

1. A new and distinct cultivar of chrysanthemum characterized particularly as to its uniqueness when compared to the unpatented cultivar Bonnie Jean by its ivory white flower color; approximately 4″-5″ less vigor and 2″ more spread when grown as a spray pot; approximately 4-5 days earlier response and 4-5 days shorter crop time; smaller and finer textured foliage; year round recommended period of use; by its absence of pollen resulting in an improved keeping quality and homelife of 4-5 days, as well as ray petals that are not marred with pollen; greater uniformity of flowering response, even when buds are initiated under low temperature; by its lack of sensitivity to present day greenhouse chemicals; improved flower substance, and improved form retention in low light periods.

No references cited.

ROBERT E. BAGWILL, Primary Examiner